United States Patent
Perriere

(10) Patent No.: US 8,105,283 B2
(45) Date of Patent: Jan. 31, 2012

(54) MINIATURIZED INJECTION DEVICE FOR MEDICAL USE

(75) Inventor: Bernard Perriere, Echirolles (FR)

(73) Assignee: Eveon, Montbonnot Saint Martin (FR)

( * ) Notice: Subject to any disclaimer, the term of this patent is extended or adjusted under 35 U.S.C. 154(b) by 6 days.

(21) Appl. No.: 12/526,973

(22) PCT Filed: Feb. 18, 2008

(86) PCT No.: PCT/EP2008/051924
§ 371 (c)(1), (2), (4) Date: Aug. 13, 2009

(87) PCT Pub. No.: WO2008/101892
PCT Pub. Date: Aug. 28, 2008

(65) Prior Publication Data
US 2010/0121271 A1    May 13, 2010

(30) Foreign Application Priority Data
Feb. 22, 2007 (FR) ..................... 07 53430

(51) Int. Cl.
*A61M 1/00* (2006.01)
(52) U.S. Cl. ..................... 604/151
(58) Field of Classification Search ............ 604/890.1, 604/131–139, 156–157, 110–111, 272, 151
See application file for complete search history.

(56) References Cited

U.S. PATENT DOCUMENTS

| 4,838,877 A | * | 6/1989 | Massau ............... 604/272 |
| 4,894,054 A | | 1/1990 | Miskinyar |
| 5,931,814 A | | 8/1999 | Alex et al. |
| 6,132,755 A | | 10/2000 | Eicher et al. |
| 6,830,560 B1 | | 12/2004 | Gross et al. |
| 6,979,316 B1 | * | 12/2005 | Rubin et al. ........... 604/156 |
| 2002/0123740 A1 | * | 9/2002 | Flaherty et al. ........ 604/890.1 |
| 2003/0083618 A1 | | 5/2003 | Angel et al. |
| 2004/0092875 A1 | | 5/2004 | Kochamba |
| 2004/0162521 A1 | * | 8/2004 | Bengtsson ............ 604/136 |

FOREIGN PATENT DOCUMENTS
WO    97/47342 A2    12/1997

OTHER PUBLICATIONS

International Search Report, mailed May 21, 2008, in corresponding International Application No. PCT/EP2008/051924, 4 pages.

* cited by examiner

*Primary Examiner* — Christopher D Koharski
(74) *Attorney, Agent, or Firm* — Sughrue Mion, PLLC

(57) ABSTRACT

The miniaturized injection device (1) for medical use comprises a tube (2) extending along a certain axis (A-A) and in which there is disposed at least one reservoir (12) for receiving a medicinal substance, the reservoir being connected to at least one needle (14). The needle is movable in the tube (2) along said axis (A-A) and the injection device (1) further includes a pump (13) interposed between the needle and the reservoir. The pump is controlled by a switch (21) that operates in response to the needle (14) moving in the tube along said axis (A-A).

16 Claims, 5 Drawing Sheets

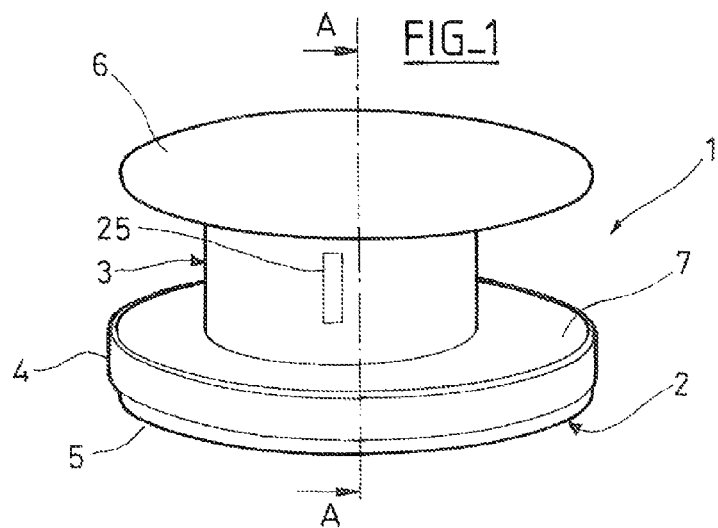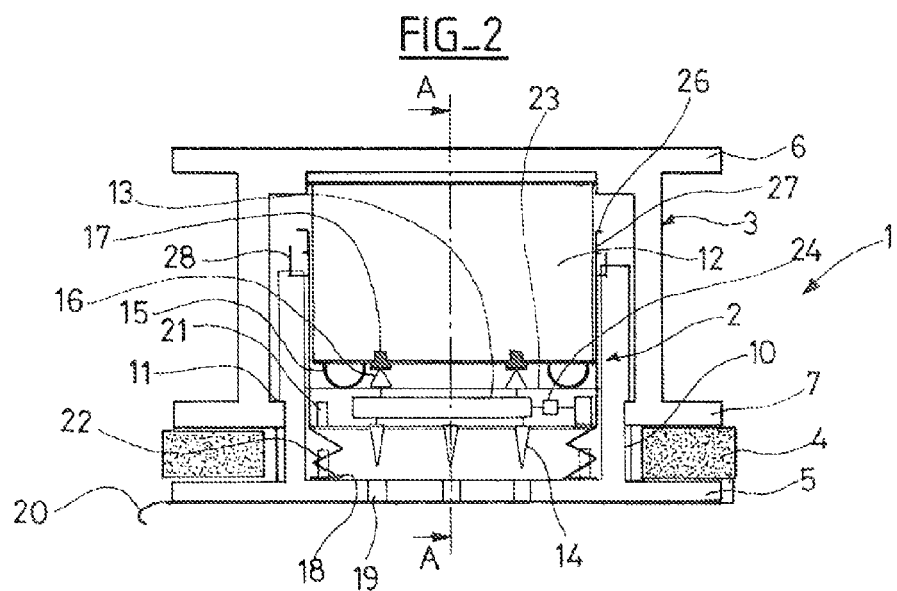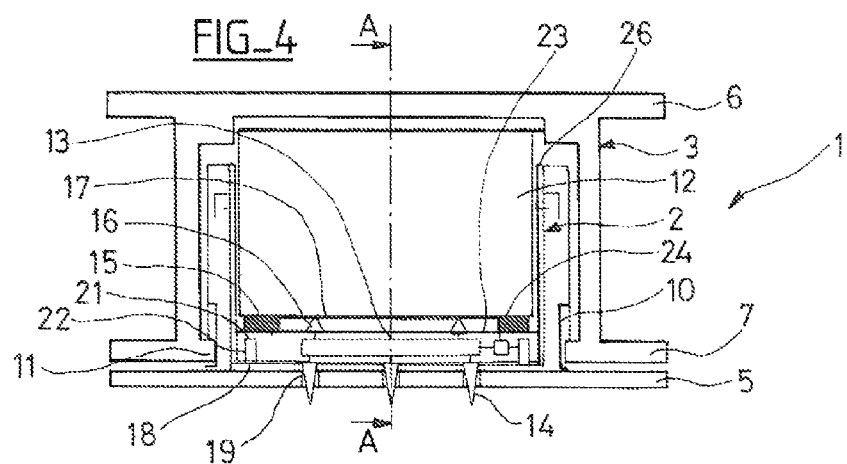

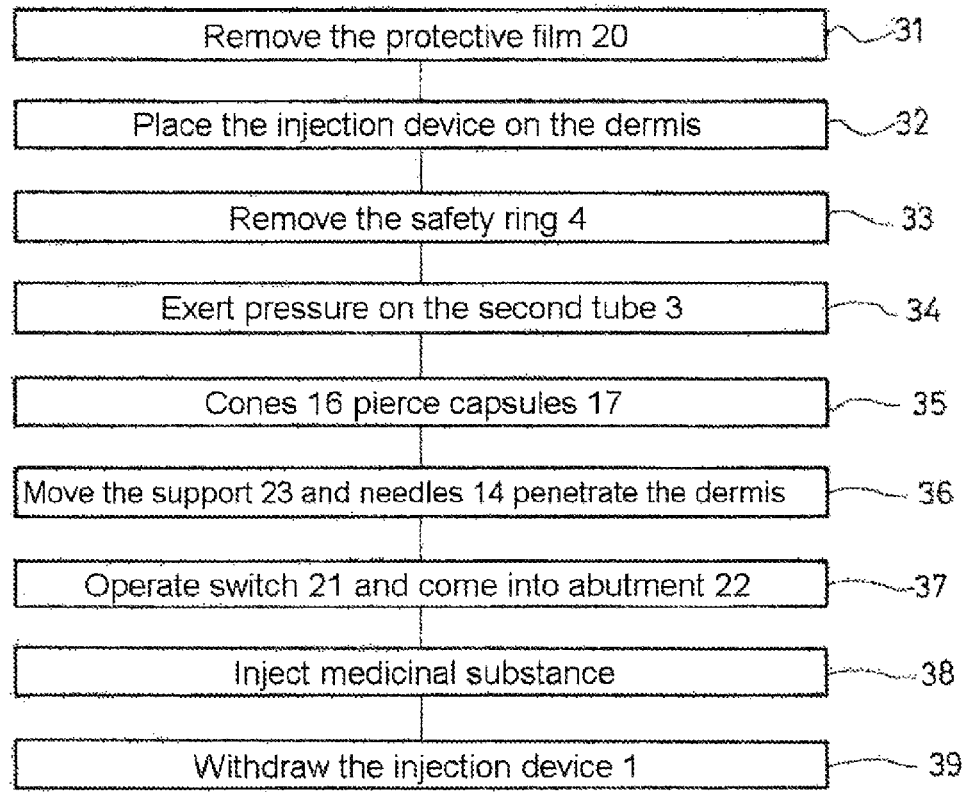
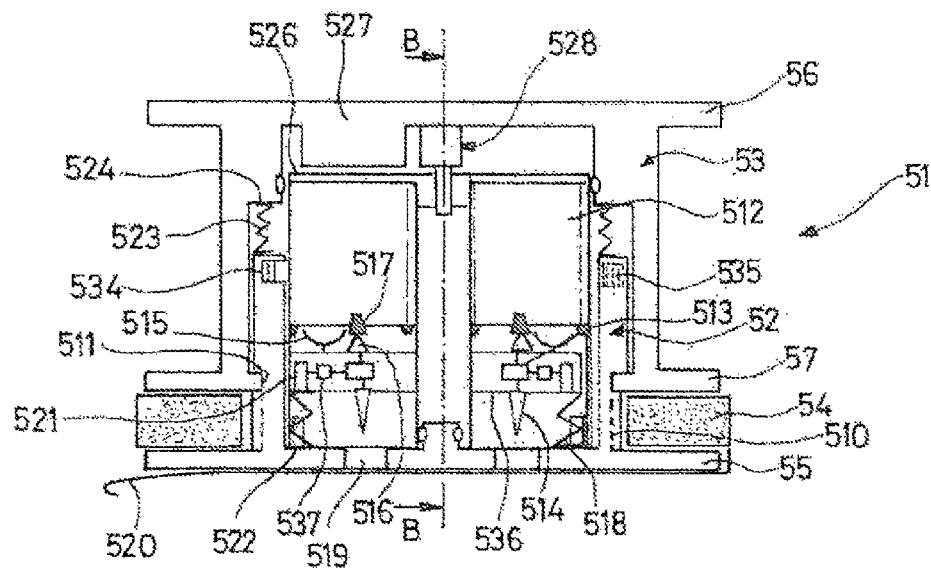

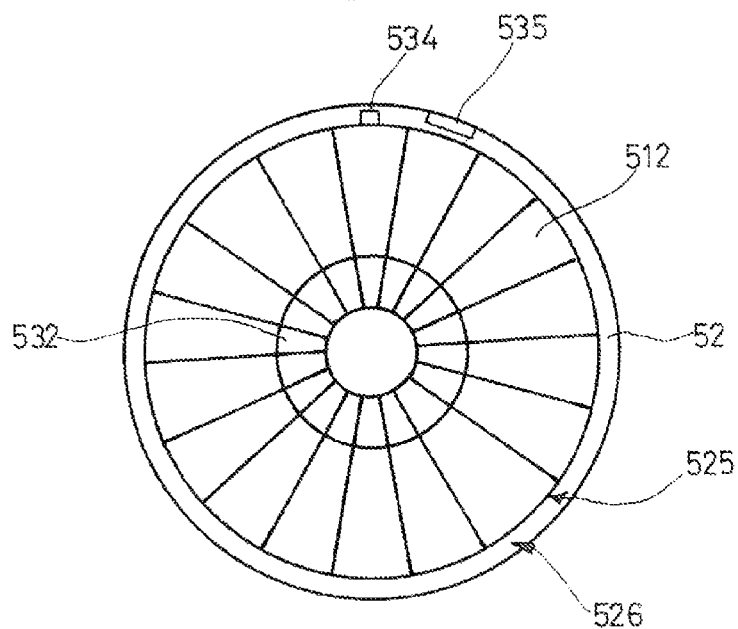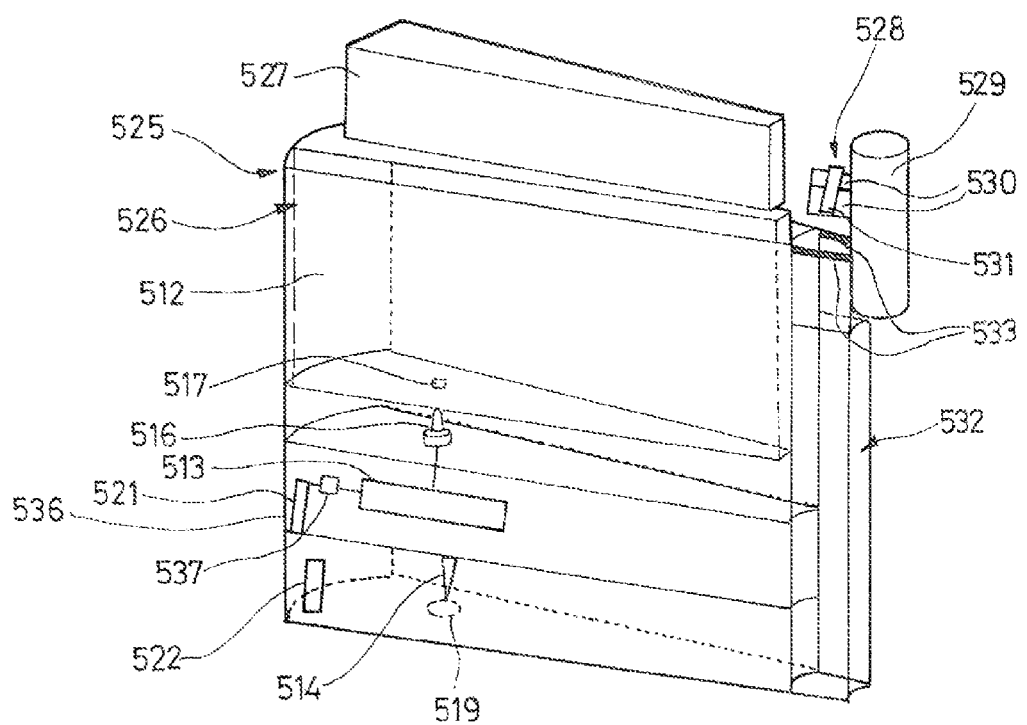

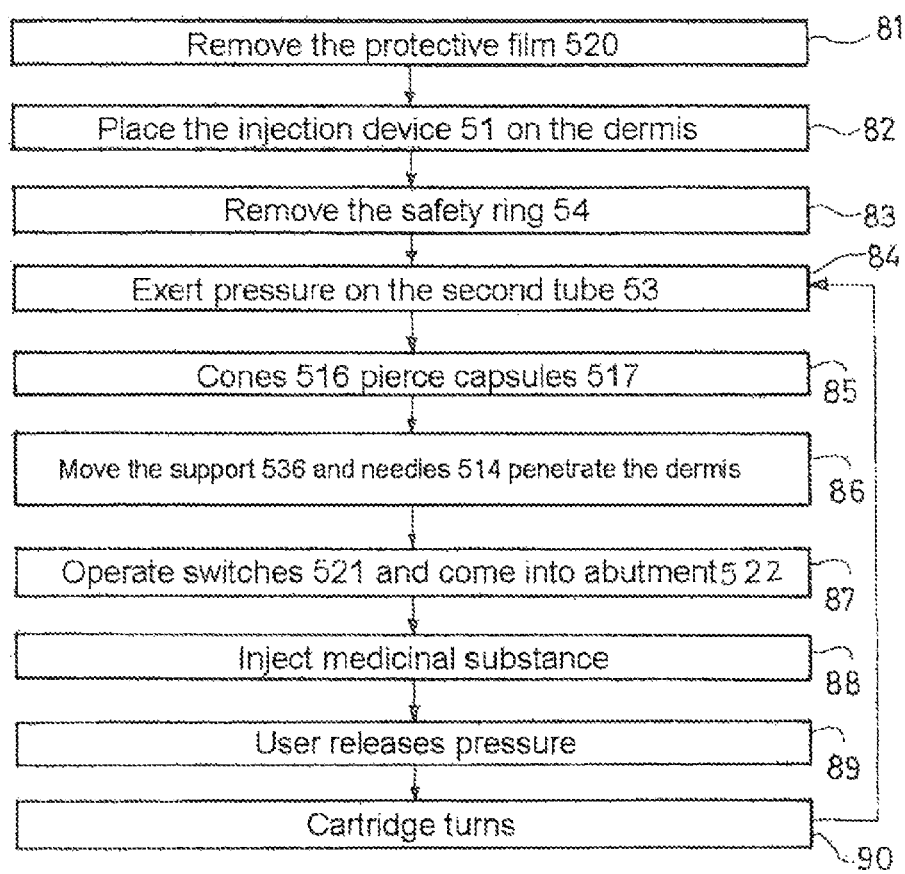
FIG_8

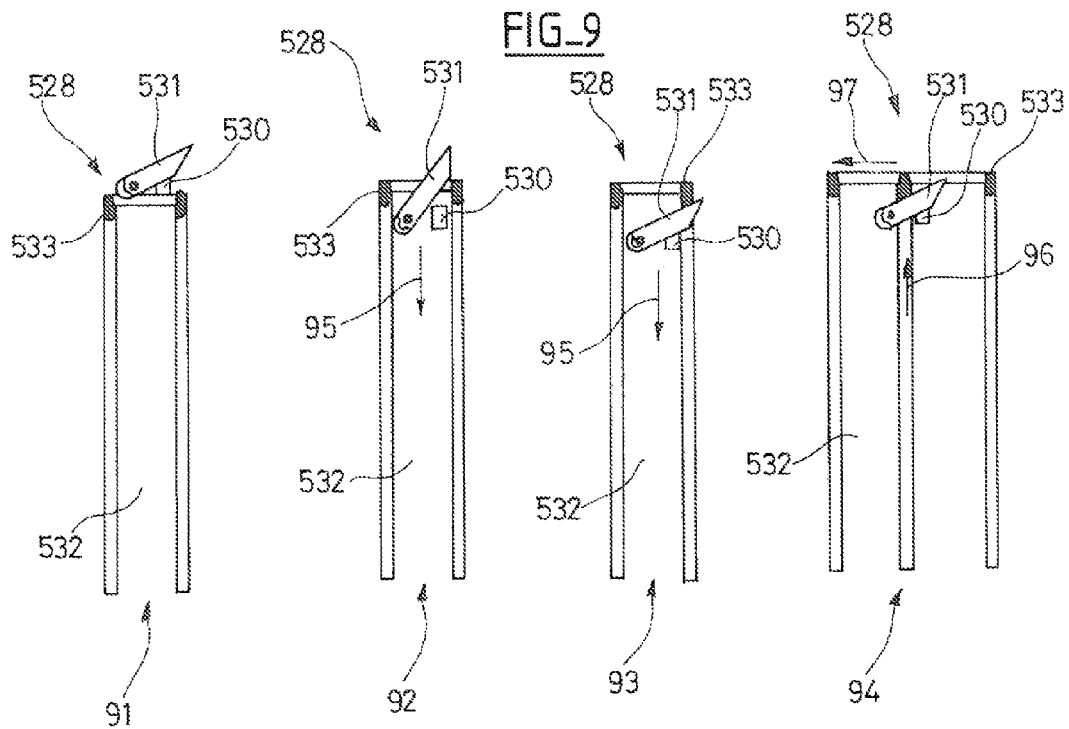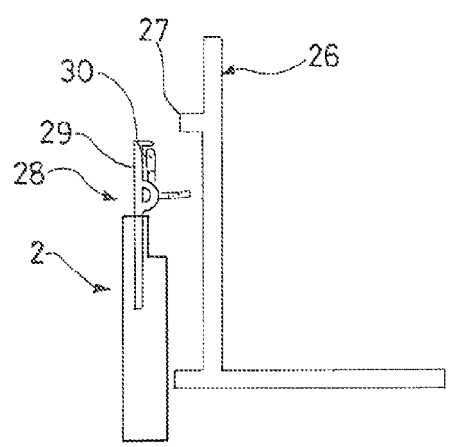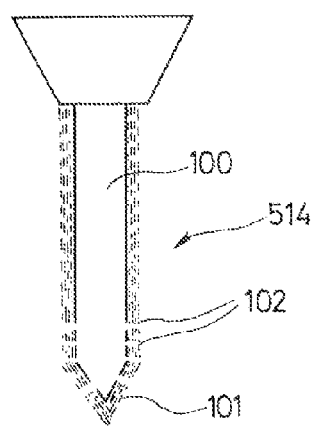

MINIATURIZED INJECTION DEVICE FOR MEDICAL USE

The invention relates to a miniaturized device for medical use that is suitable for injecting a medicinal substance subcutaneously or intramuscularly into a human being or an animal.

In particular, the invention relates to a device for medical use suitable for performing an injection without pain and without apprehension by a person on their own or with medical assistance.

In general, such transdermal devices are in the form of syringes, e.g. syringe pens, syringe carriers, or more generally injection devices that need to be held in the hand by a user.

Transdermal devices in the form of syringes have a needle that is visible and they are of dimensions that are sufficient in particular to enable the user to aim for an injection zone that is visible to the eye.

For some patients, the use of syringes can be psychologically difficult or even traumatic. Thus, mere sight of a needle can stress them and cause them to lose control. With some people, it is even impossible for them to inject themselves. This can have severe consequences for patients who are isolated, e.g. suffering from diabetes, and who require repeated injections of insulin, or in the event of unpredictable crises.

There thus exists a need for a device for injecting a medicinal substance that is sufficiently simple in use to make it possible for a patient to perform self-injection in complete safety and without apprehension.

Patent document DE 4 221 312 discloses a transdermal device suitable for making an injection. That injection device includes sensors indicating the depth at which the medicinal substance is to be injected. The injection device also includes a control system for performing the injection at the specified depth.

Such an injection device is of complex design and expensive. In addition, it is complex to use so it must be used by qualified medical personnel.

The object of the present invention is thus to present a device that is capable of performing injections to a depth suitable for the treatment, to increase patient safety, and to be capable of being used by patients themselves without apprehension. Furthermore, the injection device needs to be simple and inexpensive to manufacture.

For this purpose, the invention provides a miniaturized injection device for medical use comprising a tube extending along a certain axial direction, in which tube there is placed at least one reservoir for receiving a medicinal substance, the reservoir being connected to at least one needle, and the device being characterized in that said needle is movable in the tube along said axial direction, and in that it further comprises a pump interposed between the needle and the reservoir, the pump being controlled by means of a switch that operates in response to a movement of the needle in the tube along said axial direction.

The switch may be an electrical switch if the pump is powered electrically from a battery. It will be understood that the principle of the invention is to ensure that the switch operates to cause the pump to operate and launch automatic injection of the medicinal substance only once the needle has extended sufficiently from the tube (and has therefore penetrated far enough through the dermis, while the tubular body of the device is pressed against the dermis).

The device of the invention is a manual injection device, but it does not have a piston. It enables the movement of the needle within the tube to be adjusted so as to obtain an injection at an appropriate depth that is subcutaneous or intramuscular.

According to the invention, the needle initially moves forwards along the axial direction to move out from the tube under the effect of pressure being exerted on the tube by handling the injection device, and subsequently moves rearwards back along the axial direction to retract into the tube under the effect of the pressure exerted on the tube being released. In an advantageous embodiment, the injection device includes means for blocking movement of the needle, which means act to block movement of the needle after it has performed the two consecutive movements in the tube respectively forwards and rearwards as mentioned above, thereby making the device unusable after a first injection. In particular, the blocking means comprise an L-shaped lever mounted to pivot about the intersection between the two limbs of the L-shape.

It will thus be understood that with such blocking means, the device can be used to make an injection with the needle and the needle subsequently remains blocked inside the tube, thereby contributing to reinforcing safety in use of the device of the invention.

In a particular embodiment of the device of the invention, the pump and the needle can be mounted in a support that moves within the tube relative to the reservoir. One or more percussion cones can be provided on the support to pierce the reservoir in order to establish a flow channel between the reservoir and the pump. A reservoir with a pump and a needle can thus be assembled to form a kind of cartridge that may be removable relative to the tube. It is possible to provide a plurality of cartridges within a single tube by distributing the cartridges in a circular sector configuration.

In practice, the tube in which there are disposed a reservoir together with a pump and a needle, is itself inserted in an outer tube, these two tubes being mounted one within the other in such a manner that the needle moves within the inner tube in response to axial movement of the two tubes one relative to the other. Both tubes are provided at one end with respective radial collars that are spaced apart axially from each other when the device of the invention is in the rest state. A spacer in the form of a tearable ring can be placed between the two collars to prevent the device from operating, i.e. prevent relative movement between the two tubes and thus prevent the needle moving within the inner tube.

In the device of the invention, each needle can be designed not to have an axial vent but rather to have lateral vents only, which lateral vents are located on a helix or a circle and pass through the periphery of the needle so that the needle can pass through a sterilized felt without becoming plugged, prior to actually moving out from the inner tube.

A particular embodiment of the injection device of the invention is described in greater detail below and is shown in the drawings. The description is given by way of indicative examples only and does not limit the invention in any way.

FIG. 1 is a highly diagrammatic view of the device of the invention.

FIG. 2 shows the device in a first embodiment of the invention prior to making an injection and shown in axial section view.

FIG. 3 is a flow chart showing the operation of the FIG. 2 injection device.

FIG. 4 shows the FIG. 2 device while performing an injection.

FIG. 5 shows the device of a second embodiment of the invention in axial section view.

FIG. 6 is a plan view in radial section showing the device of the invention as shown in FIG. 5.

FIG. 7 is a detail view of a segment of the invention as shown in FIG. 5.

FIG. 8 is a flow chart showing the operation of the FIG. 5 injection device.

FIG. 9 shows the operation of the automatic rotary drive system of FIG. 5.

FIG. 10 shows a needle of the injection device of the invention.

FIG. 11 is a fragmentary view in axial section showing the blocking means of the invention.

FIG. 1 shows an embodiment of the injection device 1 of the invention, which device comprises two tubes inserted one in the other coaxially about the axis A-A, in this case two cylindrical tubes 2 and 3. At their ends shown to the bottom in FIG. 1, these two tubes are surrounded by respective collars 5 and 7 about the axis A-A, the collar 7 of the outer tube 3 (sheath tube) being axially offset relative to the collar 5 of the inner tube 2 (not visible in the figure).

As can be seen in FIG. 1, the top end of the outer tube 3 is closed by a disk 6 of diameter similar to the diameter of the collars 5 and 7. This disk serves as a thrust zone when handling the device. Furthermore, the outer tube 3 is fitted with a window 25 for viewing the quantity of medicinal substance contained in the injection device 1.

FIG. 1 shows the device 1 in the position in which it is applied against the skin of a patient. The collar 5 is thus in contact with the skin of the patient. The two collars are kept at a distance apart from each other by a spacer in the form of a safety ring 4 preventing the tube 3 from moving relative to the tube 2, and in practice preventing the tube 3 being pressed towards the contact surface formed by the collar 5 of the tube 2. The ring 4 may be designed to be torn off or it may present a breakable zone so as to enable it to be withdrawn from the device 1, e.g. by a simple pulling operation using one hand.

Clearly the tubes 2 and 3 could have a section other than circular without going beyond the ambit of the invention.

FIG. 2 shows the injection device 1 in greater detail and in section on a plane containing the axis A-A, the device 1 constituting a first embodiment that is used as a single-dose injection device. In FIG. 2, as in FIG. 1, the device 1 is shown in its state prior to being used for injection.

The first tube 2 is provided in its outer bottom portion above the collar 5 with a circumferential groove 10 in which there is received an annular projection 11 projecting radially inwards from the inner bottom portion of the second tube 3. The groove 10 extends over a certain distance along the axis A-A so that the annular projection 11 can slide in the groove 10 over said certain distance, which corresponds to the distance of movement in translation for the tube 3 relative to the tube 2 along the axis A-A.

Since the outer tube 3 is closed at its top end by the disk 6, it co-operates with the inner tube 2 to form a cavity containing a reservoir of medicinal substance 12 and a pump 13 mounted in a support 23 on which at least one needle 14 is disposed. The reservoir 12 and the support 23 are held together in the cavity by means of an outer jacket 26. The outer jacket 26 forms a sheath that keeps the reservoir 12 and the support 23 sterile. The outer jacket 26 is open both in its top portion so that part of the reservoir 12 extends out from the jacket 26, and in its bottom portion so that the needle(s) 14 likewise extend(s) out from the jacket 26. The jacket 26 is provided, on the outside of its wall, with a collar 27 for co-operating with blocking means 28 placed on the top end of the inner tube 2. The function of the blocking means 28 is to block movement of the assembly comprising the jacket 26, the reservoir 12, the support 23, and the needles 14, and is described in detail with reference to FIG. 11.

FIG. 11 shows the blocking means 28 in detail. The blocking means 28 comprise a support 29 and an L-shaped lever 30. The support 29 extends vertically and is fastened to the top end of the tube 2. The support 29 is also provided with a pivot about which the lever 30 can turn. In particular, the lever 30 pivots about an axis that is perpendicular to the longitudinal axis A-A and that passes through the intersection between the limbs constituting the L-shape. In FIGS. 2 and 11, the blocking means are shown in a state prior to blocking, i.e. the vertical limb of the L-shape is situated above the horizontal limb. In FIGS. 2 and 11, the horizontal limb of the L-shape is situated below collar 27 of the jacket 26, with the horizontal limb and the collar 27 being arranged so that moving the jacket 26 along the axis A-A causes the lever 30 to move in rotation by making contact.

The reservoir 12 may be made of glass or of a rigid plastics material. In the example of FIG. 2, the reservoir 12 is substantially cylindrical in shape and is disposed coaxially within the tube 2 at a distance from the support 23 containing the pump, a resilient element 15 acting as a spacer being placed between the reservoir 12 and the support 23 carrying percussion cones 16 pointing towards complementary capsules 17 provided in the reservoir 12. The percussion cones 16 and the capsules 17 are designed to co-operate on being moved together so as to create a passage between the reservoir 12 and the pump 13.

In FIG. 2 there can be seen a plurality of needles 14 connected to the pump 13 and mounted on the support 23 so as to point axially towards the open end of the tube 2, i.e. towards the end surrounded by the collar 5. The collar 5 also extends radially towards the inside of the tube 2 so that springs 18 interposed between the support 23 and a shoulder formed by the collar 5 oppose axial movement of the support 23 towards the collar, thereby holding the needles 4 inside the tube 2.

The collar 5 may in fact be a disk having openings 19 that are axially in alignment with the needles. These openings may be closed by a capsule 20 stuck to the disk, the capsule acting as a protective film. The function of the protective film 20 is to keep the inside of the cavity sterile, and in particular to keep the needles 14 sterile. Since the protective film 20 covers the entire surface of the disk 5, the entire surface of the disk that is to come into contact with the skin of the patient is likewise kept sterile in this way while the device is not in use. Advantageously, the protective film 20 and the safety ring 4 are fastened together so that removing either of these two from the injection device 1 causes the other to be removed as well.

Between the disk 5 and the protective film 20 it is possible to place a layer of felt (not shown) so as to cover the openings 19. The layer of felt also serves to keep the inside of the cavity sterile after the protective film has been withdrawn. The layer of felt is perforated by the needles 14 when they move axially, as described in detail below.

According to a characteristic of the invention, the support 23 is provided with a switch 21 serving to actuate the pump 13 in response to the needles 14, and thus the outer tube 3, moving axially over a certain distance. More particularly, an abutment 22 is disposed on the inside of the disk 5, and when the support 23 comes close to the abutment, the abutment causes the switch 21 to change state, thereby causing the pump 13 to operate. For this purpose, the outer jacket 26 is arranged to enable contact to be made between the switch 21 and the abutment 22, e.g. by having corresponding openings.

In this example, the pump has an electric motor that is powered by a battery 24 (e.g. a bio cell) by means of the switch 21, the battery 24 possibly also being housed in the support 23 (which may be a cylindrical support).

Alternatively, the pump may be driven by a flow of gas delivered by a gas cartridge (taking the place of a battery), in which case the switch 21 is constituted by a kind of plunger that punctures the gas cartridge so as to deliver mechanical energy to the pump 13.

The size of the injection device 1 lies in the range 2 centimeters (cm) to 5 cm in diameter and in the range 2 cm to 5 cm in height, depending on the substance to be injected. The size of the pump lies in the range 2 cm to 5 cm in width and in length, and in the range 0.5 cm to 2 cm in height, depending on the substance to be injected.

FIG. 4 shows the state of the device 1 while it is in operation for injecting a medicinal substance. In this state, the safety ring 4 and the protective film have been removed. It can be seen that the jacket 26 is in contact with the abutment 22. The percussion cones 16 have passed into the reservoir 12. The springs 18 are compressed by the effect of the tube 3 being pushed down and thus of the disk 6 being pressed against the top of the reservoir 12. The needles pass through the openings 19 after perforating the layer of felt. Since the switch 21 has changed state, the pump 13 operates to draw substance from the reservoir and deliver it to the needles 14.

In the state of FIG. 4, the lever 30 has been turned through 90°. The horizontal limb of the L-shape is situated above the vertical limb. The collar 27 of the jacket 26 is also situated below the horizontal limb of the L-shape.

FIG. 3 is a flow chart describing the succession of steps in handling and operating the device 1.

In a step 31, the user takes hold of the injection device 1 in order to remove the protective film 20.

In a step 32, the user places the injection device 1 with the collar 5 of the first tube 2 against the dermis of the patient at the location where the injection is to be made. Advantageously, the collar 5 serves to keep the dermis properly flat.

In a step 33, the user removes the safety ring 4 that was keeping the second tube 3 and the first tube 2 apart. Alternatively, if the protective film 20 and the safety ring are secured to each other, then the ring is removed in step 31 together with the film 20.

In a step 34, the user exerts a small amount of pressure on the thrust disk 6 of the second tube 3 and the axial translation movement is thus transmitted to the reservoir 12. In spite of the reservoir 12 moving in the outer jacket 26, the jacket nevertheless keeps the space between the reservoir 12 and the support 23 sterile.

In a step 35, the percussion cones 16 come into contact with the capsules 17 so as to pierce them and create a leaktight passage so that the medicinal substance contained in the reservoir 12 is transmitted to the pump 13. The percussion cones 16 are preferably surrounded by a gasket sealing the connection between the cones 16 and the capsules 17. Since the pump 13 is not in operation, the medicinal substance is kept blocked at the pump.

In a step 36, the pressure exerted by the user on the thrust disk 6 of the second tube 3 towards the first tube 2 is transmitted via the rigid reservoir 12 to the support 23 which then moves axially towards the abutment 22. The springs 18 begin to compress, and the needles 14 begin to move out from the openings 19, perforating the layer of felt and penetrating into the dermis of the patient.

Advantageously, the injection device 1 of the invention is designed so that the needles 14 penetrate to a determined depth into the dermis, or into muscle tissue when performing an intramuscular injection. The injection depth of the needles 14 is adapted to the medical treatment and is determined by the axial length of the circumferential groove 10, for example. With such an arrangement, it is possible to adapt the medicinal substance contained in the reservoir 12 and the injection depth to the desired medical treatment.

For example, when performing subcutaneous injection, the needles 14 penetrate into the dermis over a distance of 0.2 millimeters (mm) to 0.8 mm. When performing an intramuscular injection, the needles 14 penetrate over a distance of 2 mm to 3 mm.

During the step 36, the collar 27 of the jacket 26 comes to against the lever 30 of the blocking means 28. The lever 30 turns under the thrust from the collar 27 so that the collar 27 passes below the lever 30.

In a step 37, the movement of the support 23 leads to contact between the abutment 22 and the switch 21. The switch 21 changes state, thereby having the effect of causing the pump 13 to operate. Pumping is thus triggered only once the needles 14 have penetrated into the dermis or into muscle to the depth that is determined for the medical treatment. It will be understood that provision can be made, for example, for the contact to take place when the collar 7 of the second tube 3 comes into abutment against the collar 5, as shown in FIG. 4.

In a step 38, starting the pump leads to the medicinal substance being injected into the patient's body. The time required for injection varies as a function of the number of needles 14 and as a function of the volume of medicinal substance to be injected. Advantageously, the injection time can be determined by the endurance of the battery 24.

In a step 39, once the injection time has elapsed, the user releases the pressure exerted on the tube 3, thereby allowing the springs 18 to relax and retract the needles 14 into the tube 2. The collar 27 of the jacket 26 comes to bear against the lever 30 so as to turn it towards the state shown in FIG. 11. The collar 27 passes to above the lever 30 which, because of its weight, does not return to the state shown in FIG. 11, but pivots in the opposite direction until the horizontal limb of the L-shape is situated above the vertical limb, with the vertical limb bearing against the inside wall of the tube 2. Consequently, axial displacement of the reservoir 12, of the support 23, and thus of the needles is blocked by the collar bearing against the lever 30 which is prevented from moving in rotation. It will be understood that at the end of the step 39, the needles 14 are held blocked within the tube 2 by the blocking means 28. The injection device 1 can thus be handled in complete safety after it has been used.

The injection device of the invention thus constitutes means that are simple and inexpensive for performing an injection without apprehension and in complete safety. Furthermore, the device can be adapted simply to different therapeutic treatments. In particular, the medicinal substance and the depth of injection can be adapted as described above.

Advantageously, the reservoir together with the pump (the support 23) placed within the outer jacket 26 and the needle(s) constitute a kind of cartridge that can be removably mounted in the tube 2. By way of example, the cartridge can be inserted into the tube 2 by unscrewing the top of the tube 3. It is possible to envisage the cartridge being disposable while the tube 3 is designed to be recycled.

In this embodiment of the invention, the pump can be made using microfluidic micro electromechanical or mechanical systems known as MEMS or MOEMS. MEMS or MOEMS are powered for example by battery means that may be constituted by a primary cell, a bio cell, an internal fuel, or an inert gas. The duration for which power can be delivered determines the injection time. Advantageously, provision is made to ensure that the power supply lasts no longer than the time required for injecting the medicinal substance. MEMS or MOEMS are made out of materials such as silicon, glass, or injected plastics or composite materials. The pump of the injection device may, for example, be a peristaltic pump, a diaphragm pump, a centrifugal pump, a rotary pump, a flap-valve pump, or more generally any suitable technology making pumping and injection possible.

FIG. 5 is an axial section containing an axis B-B and showing an injection device 51 constituting a second embodiment of the invention, in which the device 51 is arranged to perform a plurality of repeated injections. The device 51 is also referred to as a multidose injection device. In FIG. 5, as in FIG. 1, the device 51 is shown in a state prior to being used for making an injection.

For reasons of clarity, blocking means of the kind shown in FIG. 1 are not described for this second embodiment. Nevertheless, the second embodiment could naturally be provided with such blocking means. The person skilled in the art can easily adapt the blocking means shown in FIG. 1 to the second embodiment.

The appearance of the injection device 51 is similar to the appearance of the device shown in FIG. 1. In general, the multidose injection device 51 comprises a first tube 52 inserted in a second tube 53 with a safety ring 54 disposed between the first tube 52 and the second tube 53. In the embodiment of FIG. 5, the tubes 52 and 53 are cylindrical.

These two tubes are surrounded at their bottom ends in FIG. 5 by two collars 55 and 57 about the axis A-A, the collar 57 of the outer tube 53 (sheath tube) being offset axially relative to the collar 55 of the inner tube 52.

As can be seen in FIG. 5, the top end of the outer tube 53 is closed by a disk 56 of diameter similar to the diameter of the collars 55 and 57. The disk serves as a thrust zone for manipulating the device.

The collar 55 is designed to come into contact with the skin of the patient. The two collars are held at a distance apart from each other by a spacer in the form of a safety ring 54 that prevents the tube 53 moving relative to the tube 52, and in practice prevents the tube 53 being pressed towards the contact surface formed by the collar 55 of the tube 52. The ring 54 may be designed to be torn off or it may present a breakable zone so as to be capable of being withdrawn from the device 51 merely by being pulled off using a single hand, for example.

As described in greater detail below, once the safety ring 54 has been withdrawn, the second tube 53 and the first tube 52 are held apart by means of a return spring 523 disposed between the top edge of the cylindrical shape of the first tube 52 and a shoulder 524 formed inside the cylindrical shape of the second tube 53.

It is clear that the tubes 52 and 53 could be of a section other than circular without going beyond the ambit of the invention.

The first tube 52 is provided in its outer bottom portion, above the collar 55, with a circumferential groove 510 in which there can be received an annular projection 511 that projects radially from the inside bottom portion of the second tube 53. The groove 510 extends over a certain distance along the axis B-B so that the annular projection 511 can slide in the groove 510 over a certain distance that corresponds to the distance through which the tube 53 can be moved in translation relative to the tube 52 along the axis B-B.

Since the top portion of the outer tube 53 is closed by the disk 56, it co-operates with the inner tube 52 to form a cavity containing a reservoir of medicinal substance 512, and a pump 513 mounted in a support 536 having at least one needle 514 placed thereon.

Thus, each reservoir 512 associated with one or more corresponding needles 514 and with a corresponding pump 513 forms a self-contained and independent cartridge 526. The injection device 51 has a plurality of cartridges 526, each having a section in the form of a circular sector, which cartridges are distributed around the longitudinal axis B-B of the injection device 51, as shown in FIG. 6. The cartridges 526 are placed in a support system 525 capable of turning about the longitudinal axis B-B. In addition, the support system 525 is removable from the tubes 52 and 53 so as to constitute a consumable item that can be renewed.

In FIG. 5, there can be seen the thrust disk 56 provided on its inside portion with a shoulder 527 that is disposed so as to bear against the reservoir 512 of only one segment.

The reservoir 512 may be made of glass or of a rigid plastics material. In the example of FIG. 5, the reservoir 512 is in the form of a circular sector disposed at a distance from the support 536 containing the pump, a resilient element 515 serving as a spacer being disposed between the reservoir 512 and the support 536 that is fitted with percussion cones 516 pointing towards complementary capsules 517 disposed in the reservoir 512. The percussion cones 516 and the capsules 517 are designed to co-operate with one another when they are moved together so as to create a passage between the reservoir 512 and the pump 513.

FIG. 5 shows a needle 514 connected to the pump 513 and mounted on the support 536 so as to point axially towards the open end of the tube 52, i.e. the end surrounded by the collar 55. The collar 55 also extends radially towards the inside of the tube 52 so that springs 518 interposed between the support 536 and a shoulder formed by the collar 55 oppose axial movement of the support 536 towards the collar, and thus keep the needles 514 inside the tube 52.

The collar 55 may, in fact, be constituted by a disk having openings 519 that are in axial alignment with the needles. These openings can be closed by a capsule 520 that is stuck onto the disk, which capsule acts as a protective film. The function of the protective film 520 is to keep the inside of the cavity, and in particular the needles 514, sterile. Since the protective film 520 covers the entire surface of the disk 55, the entire surface of the disk for coming into contact with the skin of the patient is likewise kept sterile in this manner while the device is not in use.

According to a characteristic of the invention, the support 536 is fitted with a switch 521 serving to actuate the pump 513 in response to a certain amount of axial movement of the needles 514 and thus of the outer tube 53. More particularly, an abutment 522 is placed on the inside of the disk 55, and when the support 536 comes close to said abutment, it causes the switch 521 to change state, thereby putting the pump 513 into operation.

FIG. 7 shows in detail a cartridge 526 comprising a reservoir 512 associated with a pump 513 and a needle 514.

The top surface of the reservoir 512 presses against the shoulder 527 of the second tube 53. As shown in FIG. 7, the shoulder 527 matches the shape of the top surface of the reservoir 512 so that movement of the second tube 53 acts on one cartridge 526 only.

In the state shown in FIGS. 5 and 7, prior to the injection device 51 being used, the cone 516 is kept at a distance from the capsule 517 by the resilient element 515.

When the pump 513 is an electric pump, the support 536 is also provided with a battery 537. The battery 537 is connected to the pump 513 and to the switch 521 so that operating the switch has the effect of delivering electricity to the pump. By way of example, the battery 537 is a bio cell.

Alternatively, the pump may be driven by a flow of gas delivered by a gas cartridge (taking the place of a battery), with the switch 521 then being a kind of plunger that perforates the gas cartridge on being operated, thereby delivering mechanical energy to the pump 513.

The repeated injection device 51 also includes an automatic rotary drive system 528 for turning the cartridges 526 about the axis, so that after each injection of a medicinal substance coming from one particular cartridge, the support 525 is caused to rotate so that a new cartridge 526, and thus a new reservoir full of medicinal substance, moves into position facing the shoulder 527.

The rotary drive system 528 is secured to the second tube 53 and comprises: a central shaft 529; two radial paddles 530; and a rod 531. The central shaft 529 is placed at the center of the thrust disk 56 and inside the second tube 53. This central shaft 529 extends the paddles 530 radially. The rod 531 is fastened in rotary manner to one of the paddles 53 and rests against the other paddle so as to be inclined relative to a horizontal direction.

Furthermore, the support 525 has a central core 532 that surrounds the central shaft 529. The central core 532 has only two radial fins 533 in its top portion for the purpose of co-operating with the rotary drive system 528, as shown in detail with reference to FIG. 9.

Rotation of the support 525 is stopped by means of a lug 534 disposed on the cylindrical outer wall of the support 523 that comes to bear against the abutment 535 placed on the cylindrical inner wall of the first tube 52.

FIG. 8 is a flow chart for describing the operation of the repeated injection device 51.

In a step 81, the user takes hold of the injection device 51 to remove the protective film 520 and thus reveal the needles 514.

In a step 82, the user places the injection device 51 with the collar 55 of the first tube 52 against the dermis of the patient at the location where the injection is to be made. Advantageously, the function of the collar 55 is to hold the dermis flat at a suitable distance from the needles 514. Consequently, the medicinal substance is always injected to the depth that is appropriate for the treatment.

In a step 83, the user removes the safety ring 54 that keeps the second tube 53 apart from the first tube 52.

The step 83 corresponds to the state 91 of the automatic rotary drive system 528 shown in FIG. 9. In this state 91, the rod 531 is fastened in rotary manner to one of the paddles 530 and rests against the other paddle so as to be inclined relative to a horizontal direction. In addition, the rod 531 and the paddles 530 are situated above the fins 533.

In a step 84, the user exerts light pressure on the thrust disk 56, thereby urging the second tube 53 towards the first tube 52. The movement in axial translation along B-B is thus transmitted to the particular reservoir 512 that is in contact with the shoulder 527. The return spring 523 compresses under the pressure exerted.

Step 84 corresponds to state 92 of the automatic rotary drive system 528 shown in FIG. 9. In state 92, the paddles 530 are situated below the fins 533. However, one portion of the rod 531 is situated above the fins 533, while its other portion is situated below. It will be understood that the movement of the second tube 53 in step 84 gives rise to movement of the paddles 530 and of the rod 531 between the fins 533 of the segment in the direction of arrow 95. The direction of arrow 95 represents the movement of the second tube 53 towards the first tube 52. Furthermore, between the states 91 and 92, the rod 531 has turned about the paddle 530 and no longer rests on the other paddle 530, but on one of the fins 533.

In a step 85, the percussion cone 516 comes into contact with the capsule 517 so as to pierce it and create a leaktight passage for the medicinal substance contained in the reservoir 512 for transmission to the pump 513. The percussion cones 516 are preferably surrounded by a gasket for sealing the connection between the cones 516 and the capsules 517. Since the pump 513 is not in operation, the medicinal substance is kept blocked at the pump.

In a step 86, the pressure exerted by the user on the thrust disk 56 of the second tube 53 towards the first tube 52 is transmitted via the shoulder 527 and via the rigid reservoir 512 to the support 536 which then moves towards the collar 55 of the first tube 52. The springs 518 begin to compress. The needles 514 begin to move out through the openings 519 and penetrate into the dermis of the patient.

Advantageously, the injection device 51 of the invention is designed so that the needles 514 penetrate to a determined depth in the dermis or into muscle tissue when performing an intramuscular injection. The injection depth of the needles 514 is adapted to the medical treatment and is determined, for example, by the axial length of the circumferential groove 510. With such an arrangement, it is possible to adapt the medicinal substance contained in the reservoir 512 and the depth of injection depending on the desired medical treatment.

Step 86 corresponds to state 93 of the automatic rotary drive system 528 shown in FIG. 9. In step 93, the paddles 530 are still situated beneath the fins 533. However, the rod 531 is situated entirely beneath the fins 533.

As in step 84, the movement of the second tube 53 in step 86 causes the paddles 530 and the rod 531 between the fins 533 of the segment to move in the direction of arrow 95. Consequently, between the states 92 and 93, the rod 531 has turned about the paddle 530 and now rests in inclined manner against the other paddle 530. In addition, the rod 531 projects laterally outside the space formed between the two fins 533.

In a step 87, the movement of the support 536 causes the switch 521 to come into contact with the abutment 522. The switch 521 operates, thereby causing the pump 513 to operate. Pumping is thus triggered only once the needle 514 has penetrated into the dermis or into the muscle to the depth determined for the medical treatment. It can be understood that provision may be made for contact to take place when the collar 57 of the second tube 53 comes into abutment against the collar 55.

Consequently, in step 87, the percussion cones 516 have passed through the capsules 517, the resilient member 515 and the return springs 518 and 523 are compressed, the needles 514 have passed through the openings 519, and the abutment 522 is in contact with the switch 521. It is in this state of the injection device 51 that injection can begin.

In a step 88, the triggering of pumping leads to the medicinal substance being injected from the reservoir 512 towards the needles 514, and from the needles 514 into the body of the patient. The duration of injection varies as a function of the number of needles 514 and as a function of the volume of medicinal substance to be injected. Advantageously, the duration of injection is determined by the lifetime of the battery 537.

In a step 89, once the injection time has elapsed, the user releases the pressure exerted on the second tube 53, the needles 514 retract into the first tube 52 under the effect of the return springs 518, and the second tube 53 moves away from the first tube 52 under drive from the return spring 523. The injection device 51 can thus be handled in complete safety after a first injection.

The step 89 corresponds to the state 94 of the automatic rotary drive system 528 shown in FIG. 9. In state 94, the paddles 530 are still situated beneath the fins 533. However, the inclined rod 531 pushes the fin 533 in the direction of arrow 96. The direction of arrow 96 represents the movement of the second tube 53 going away from the first tube 52.

Advantageously, the combination of thrust in the direction of arrow 96 and the inclination of the rod 531 gives rise in step 90 to the cartridge 526 turning about the longitudinal axis B-B of the support 525. FIG. 9 shows the movement of the cartridges in the direction of arrow 97.

The paddles 530 and the rod 531 rise vertically in the direction of arrow 96 until they pass into the space formed between the following two fins 533, i.e. the two fins of the next following cartridge.

At the end of step 90, the automatic rotary drive system 528 is back in the state 91 and a new reservoir 512 of a new cartridge faces the shoulder 527. The repeated injection device 51 is ready to make a new injection in step 84. It can thus be understood that with such a device it is possible to make one or more injections in succession to an appropriate depth.

The lug 534 and the abutment 535 are placed in such a manner that the turning of the cartridge is stopped once the medicinal substance has been injected from the last reservoir, thereby preventing further use of the injection device.

The reservoirs 512 may contain medicinal substances that are different or identical, depending on the desired therapeutic treatment.

The size of the repeated injection device 51 lies in the range 3 cm to 7 cm in width and in length, and in the range 2 cm to 5 cm in height, depending on the substance to be injected. The size of the pump lies in the range 0.2 cm to 1 cm in width and in length, and in the range 1 cm to 5 cm in height depending on the substance to be injected.

FIG. 10 shows a needle 14 or 514 of the injection device of the invention.

As is well known, a needle generally comprises a hollow shank 100 of cylindrical shape with a conical shape 101 at its end for penetrating first into the dermis.

In particular, the needle of the injection device of the invention has vents 102 passing right through the wall of the needle 514 and disposed in the sides of the needle, i.e. along the hollow shank 100, or at the edge of the conical shape 101, but not at its tip. These vents 102 are for passing the medicinal substance from inside the needle towards the outside, and in particular into the human body.

Such a needle without an end opening, i.e. with a conically-shaped tip 101, makes it possible to cause the needle to penetrate into the dermis without blocking its opening. This improves injection flow rate.

Depending on the therapeutic application, the vents may be more or less numerous and they may be distributed over the needle so as to form circles or spirals, for example.

Advantageously, the invention provides for the needle to have a microporous surface, e.g. for the purpose of retaining disinfectant and/or anesthetic and/or healing substances. Alternatively, microgrooves may be formed in the outside surface of the needle.

The needles 514 are preferably of a length that lies in the range 0.5 mm to 3 mm, with a diameter that lies in the range 0.2 mm to 0.8 mm depending on the application. The needles may be made out of various materials, for example out of stainless steel, steel alloys, injected plastics materials, composite materials, or ceramics.

The invention claimed is:

1. A miniaturized injection device (1; 51) for medical use comprising two tubes (2; 52; 3, 53) extending along a certain axial direction (A-A; B-B), a first tube (2; 52) inserted in a second tube (3; 53) with which it cooperates to form a cavity, in which second tube (3; 53) there is placed at least one reservoir (12; 512) for receiving a medicinal substance, the reservoir (12; 512) being connected to at least one needle (14; 514) disposed on a support (23) axially movable within said first tube (2; 52) in such a manner that said needle (14; 514) is moved axially in said first tube (2; 52) in response to axial movement of said second tube (3; 53) relative to said first tube (2; 52), and the miniaturized injection device (1; 51) being characterized in that, it is arranged in order that, in a step, the pressure exerted on said second tube (3; 53) and the axial translation movement of said second tube (3; 53) is transmitted to said reservoir (12; 512), said needle (14; 514) and said support (23), said needle (14; 514) being therefore movable in said first tube (2; 52) along said axial direction (A-A; B-B), and in that it further comprises a pump (13; 513) interposed between said needle (14; 514) and said reservoir (12; 512), said pump (13; 513) being controlled by means of a switch (21; 521) that operates, in a further step, in response to said axial translation movement of said needle (14; 514) and said reservoir (12; 512) and said support (23) in said first tube (2; 52) along said axial direction (A-A; B-B), leading to contact between an abutment (22) and said switch (21; 521), said switch (21; 521) being able to change state, thereby having the effect of causing said pump (13; 513) to operate and leading in again a further step to the medicinal substance being injected into the patient's body.

2. An injection device according to claim 1, in which the needle (14; 514) initially moves forwards along said axial direction (A-A; B-B) so as to move out from the tube (2; 52), and then rearwards back along said axial direction (A-A; B-B) in order to retract into the tube (2; 52), the injection device including blocking means (28) for blocking movement of the needle (14; 514) and that act to block movement of the needle (14; 514) after it has moved twice in the tube (2; 52) respectively forwards and rearwards.

3. An injection device according to claim 2, in which the blocking means comprises an L-shaped lever (30) pivotally mounted at the intersection between limbs of the L-shape.

4. An injection device according to claim 1, in which said pump (13; 513) is an electric pump powered by an electric motor connected to a battery (24; 537) via said switch (21; 521).

5. An injection device according to claim 1, in which the needle (14; 514) is movable axially as far as an abutment (22; 522), and in which the switch (21; 521) is operated when the needle (14; 514) comes into abutment.

6. An injection device according to claim 1, in which the pump (13; 513) is mounted in a needle support (23; 536) that is movable axially within the tube, at least one spring (18, 518) being provided in the tube to oppose movement of the support (23; 536) in the tube (2; 52).

7. An injection device according to claim 1, in which said reservoir (12; 512) is movable axially relative to the needle (14; 514) in the tube, and in which the reservoir (12; 512) is connected to the pump (13; 513) via at least one percussion cone (16; 516).

8. An injection device according to claim 1, in which said tube (2; 52) is an inner tube inserted in an outer tube (3; 53) disposed coaxially about said inner tube, in such a manner that the needle (14; 514) is moved axially in the inner tube in response to axial movement of the outer tube relative to the inner tube.

9. An injection device according to claim 8, in which said inner and outer tubes present respective first and second collars (5, 7; 55, 57) about the axis, and in which a removable spacer (4; 54) is interposed between the two collars (5, 7; 55, 57) to block relative axial movement of one tube relative to the other.

10. An injection device according to claim 1, in which the reservoir (12) with the pump (13) and the needle (14) are assembled together to form a cartridge.

11. An injection device according to claim 1, characterized in that it includes a plurality of cartridges (526).

12. An injection device according to claim 11, in which said cartridges (526) present respective sections in the form of circular sectors and are distributed around the longitudinal axis (B-B).

13. An injection device according to claim 11, characterized in that said cartridges (526) are disposed in a support system (525) that is rotatable about the longitudinal axis (B-B).

14. An injection device according to claim 1, in which each needle (14; 514) has one or more vents (102) that are disposed laterally relative to the needle.

15. An injection device according to claim 14, in which said vents (102) are disposed in a circular or a spiral configuration.

16. An injection device according to claim 1, in which said reservoir (12; 512) is rigid.

\* \* \* \* \*